United States Patent [19]

Noceti et al.

[11] Patent Number: 5,720,858
[45] Date of Patent: Feb. 24, 1998

[54] METHOD FOR THE PHOTOCATALYTIC CONVERSION OF METHANE

[75] Inventors: Richard P. Noceti; Charles E. Taylor; Joseph R. D'Este, all of Pittsburgh, Pa.

[73] Assignee: The United States of America as represented by the United States Department of Energy, Washington, D.C.

[21] Appl. No.: 682,498

[22] Filed: Jul. 17, 1996

[51] Int. Cl.$^6$ ............................ C07F 1/00; C07C 29/00; C07B 41/00
[52] U.S. Cl. ............................ 204/157.6; 204/157.9; 568/950
[58] Field of Search ............................ 204/157.6, 157.9; 568/950

[56] References Cited

U.S. PATENT DOCUMENTS

| | | | |
|---|---|---|---|
| 4,769,504 | 9/1988 | Noceti et al. | 585/415 |
| 4,917,784 | 4/1990 | Shelnutt | 204/157.6 |
| 5,019,652 | 5/1991 | Taylor et al. | 562/549 |
| 5,104,504 | 4/1992 | Tanaka et al. | 204/157.9 |

OTHER PUBLICATIONS

Ogura et al., "Photochemical Conversion of Methane", J. of Molecular Catalysis, vol. 43, pp. 371–379, 1988.
Ashokkumar et al., "Factors Influencing the Photocatalytic Efficiency of WO3 particles", J. of Photochem. and Photobio., A: Chem., vol. 49, pp. 249–258, 1989.
Maruthamuthu et al., "Hydrogen production from water in visible light with undoped/doped WO3 semiconductor powders and colloids", Bulletin of Electrochemistry 6(1) Jan. 1990, 128–131.
Taylor et al., "Recent On-site Research in the Conversion of Methane", (1994) Month Unavailable.
Ashokkumar and Maruthamuthu, "Photocatalytic Hydrogen Production with Semiconductor Particulate Systems: An Effort to Enhance the Efficiency", Int. J. Hydrogen Energy, 16, (9) pp. 591–595, (1991) Month Unavailable.
Maruthamuthu et al., "Visible Light Induced Hydrogen Production with Ca(II)/Bi)3 and Pt/Bi2O3/RuO2 from Aqueous Methyl Viologen Solution", Adv. Hydrogen Energy 8 (2) (1990) Month Unavailable.
Maruthamuthu and Ashokkumar, "Doping Effects of Transition Metal Ions on the Photosensitization of WO3 Particles", Solar Energy Materials 17 (1988) 433–438 Month Unavailable.
Ashokkumar and Maruthamuthu, "Preparation and characterization of doped WO3 photocatalytic powders", (1989) Month Unavailable.
Maruthamuthu and Ashokkumar, "Hydrogen Generation Using Cu(II)WO3 and Oxalic Acid By Visible Light" Int. J. Hydrogen Energy, 13, (11) pp. 677–680, (1988) Month Unavailable.
Maruthamuthu et al., "Hydrogen evolution from Water With Visible Radiation in Presence of Cu(II)WO3 and Electron Relay" No Date Available.
Maruthamuthu and Ashokkumar, "Hydrogen Production with Visible Light Using Metal Loaded–WO3 and MV2+ in Aqueous Medium" Int. J. Hydrogen Energy, 14, (4) pp. 275–277, (1989) Month Unavailable.
Borgarello et al. "Visible Light Induced Water Cleavage in Colloidal Solutions of Chromium–Doped Titanium Dioxide Particles", J. Am. Chem. Soc. (1982) 104, 2996–3002 Month Unavailable.
Nenadovic et al. "Electron Transfer Reactions and Flat–Band Potentials of WO3 Colloids", J. Phys. Chem. (1984) 88, Month Unavailable 5827–5830.

*Primary Examiner*—Kathryn L. Gorgos
*Assistant Examiner*—Edna Wong
*Attorney, Agent, or Firm*—Mark P. Dvorscak; Mark LaMarre; William R. Moser

[57] ABSTRACT

A method for converting methane to methanol is provided comprising subjecting the methane to visible light in the presence of a catalyst and an electron transfer agent. Another embodiment of the invention provides for a method for reacting methane and water to produce methanol and hydrogen comprising preparing a fluid containing methane, an electron transfer agent and a photolysis catalyst, and subjecting said fluid to visible light for an effective period of time.

19 Claims, 3 Drawing Sheets

5,720,858

METHOD FOR THE PHOTOCATALYTIC CONVERSION OF METHANE

CONTRACTUAL ORIGIN OF THE INVENTION

The United States Government has rights to this invention pursuant to employee/employer relationship of the inventors to the U.S. Department of Energy at the Pittsburgh Energy Technology Center.

BACKGROUND OF THE INVENTION

1. Field of the Invention

The present invention relates to a method for converting methane into methanol, and more particularly, the present invention relates to a method for converting methane and water to methanol and hydrogen using visible light and a catalyst.

2. Background of the Invention

The importance of methanol as a feedstock chemical and as a fuel is undeniable. Methanol can be derived from methane, of which the world has vast proven reserves.

A myriad of techniques for methane conversion exist. One such method involves the partial oxidation of methane to methanol, wherein methane is first converted to carbon monoxide and hydrogen for later synthesis into methanol. Currently, the processes for the direct oxidation of methane to methanol suffers from low methane conversion and poor methanol selectivity.

Other methane to methanol conversion techniques, such as that disclosed by K. Ogura and M. Kataoka in the *Journal of Molecular Catalysis* 4 3 (1988) pp 371–379, require ultraviolet (UV) radiation of approximately 185 nanometers (nm) and special photochemical reactors. Such UV requirements impose special health and equipment factors.

Catalysts have been utilized in conjunction with visible light to produce hydrogen, as disclosed by P. Maruthamuthu et al., *Bulletin of Electrochemistry* 6 (1) January 1990, pp. 128–131. However, neither this nor any other methods teach a method for direct conversion of methane to methanol in high yields.

A need exists in the art for a method for converting methane to methanol using widely available reactants and without special equipment. The method should be performed at normal pressures, using harmless radiation wavelengths, and result in high product yields.

SUMMARY OF THE INVENTION

An object of the present invention is to provide a method for converting methane to methanol that overcomes many of the disadvantages of the prior art.

Another object of the present invention is to provide a simple method for converting methane to methanol. A feature of the invention is the use of visible light to facilitate the conversion process. An advantage of the present invention is the minimization of health and environmental risks associated with the conversion process.

Yet another object of the present invention is to provide a method for converting methane to methanol and hydrogen. A feature of the invention is the use of readily available materials such as sun light, water and methane as reactants and in mild reaction conditions. An advantage of the invention is the minimization of costs for conversion.

Briefly, the invention provides for a method for converting methane to methanol comprising subjecting the methane to visible light in the presence of a catalyst and an electron transfer agent.

Another embodiment of the invention provides for a method for reacting methane and water to produce methanol and hydrogen comprising preparing a fluid containing methane, an electron transfer agent and a photolysis catalyst, and subjecting said fluid to visible light for an effective period of time.

BRIEF DESCRIPTION OF THE DRAWINGS

These and other objects and advantages of the present invention will become readily apparent upon consideration of the following detailed description and attached drawing, wherein.

DETAILED DESCRIPTION OF THE INVENTION

The present invention teaches a novel pathway for the direct conversion of methane to methanol under mild conditions, using light, water and a semi-conductor catalyst. The use of visible light instead of UV light greatly simplifies reactor design and permits flexibility in the selection of a light source.

Reaction Scheme #1, infra, depicts the electron transfer between reactants in the invented process. The process initially produces a hydroxyl radical with the aid of a semi-conductor catalyst and an electron transfer molecule. The newly generated hydroxyl radicals then react with methane to produce a methyl radical. The methyl radical then reacts with additional water to produce methanol and hydrogen.

Specifically, step one of the scheme depicts a semi-conductor catalyst, such as transition metal oxide (e.g. tungsten oxide ($WO_3$)), which is doped with a suitable metal such as copper (Cu), platinum (Pt) or lanthanum (La), being irradiated with light of the visible spectrum (i.e. above 400 nm). This irradiation excites an electron out of the valance band of the catalyst's orbital structure, leaving a positive hole $h+_{VB}$. The excited electron $e-_{CB}$ resides in the conduction band of the catalyst's orbital structure.

As can be noted in step two of Reaction Scheme #1, $e-_{CB}$ reacts with an electron transfer agent (e.g. methyl viologen dichloride hydrate $MV^{2+}$) to create the electron transfer radical MV.+. Step three of Reaction Scheme #1 depicts the positive hole $h+_{VB}$ attracting the hydroxyl anion to effectively split water, leaving a proton.

REACTION SCHEME #1

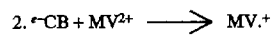

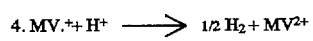

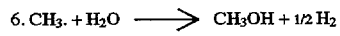

Step four of Reaction Scheme #1 utilizes the charge from the proton to regenerate the +2 charged methyl viologen dichloride hydrate and a half mole of hydrogen gas. Step five of Reaction Scheme #1 depicts methane reacting with the hydroxyl ion, which was first generated in step three, to produce a methyl radical and water. The final step (step 6) of Reaction Scheme #1 depicts the methyl radical reacting with water to form methanol and an additional half mole of hydrogen gas.

Figure 1:
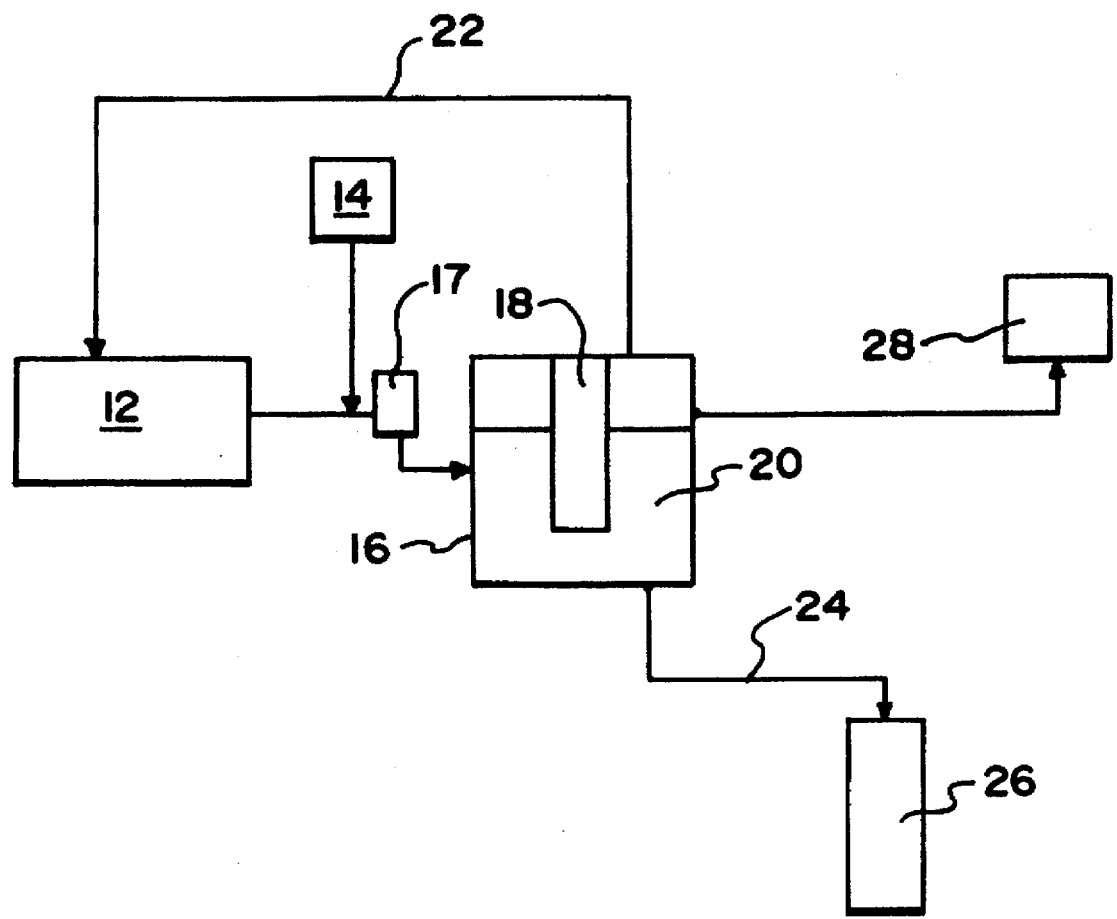
FIG. 1 is a schematic diagram of the invented method, in accordance with the present invention.

Generally, the invented method is depicted as numeral 10 in FIG. 1. Methane, directed from a methane supply 12, is first mixed with water 14. The methane-water mixture enters a reaction chamber 16 that contains a light source 18. The methane-water mixture now mixes with an electron transfer agent and a photolytic catalyst to create a reaction fluid 20. While the electron transfer agent is selected to be miscible with water, photolytic catalyst is kept suspended in the fluid via stirring, mechanical suspension, or other type of method.

The reaction fluid 20 is then subjected to light selected from a range of wavelengths for a period of time to effect conversion of methane to methanol and hydrogen gas. Preferably, the reaction fluid is subjected to light for a period of time between approximately 1 second and 5 minutes. Product streams exiting the reaction chamber 16 can be passed through a chiller or other type of heat exchanger such as a cold trap operating at approximately 0° C. The hydrogen gas is collected in a gas collection device 28 while the liquid methanol is separated from the reaction fluid and directed to a methanol collector 26. Unconverted methane is shunted back to the main methane supply via a feedback loop 22. Hydrogen can be separated from the excess methane via known processes, one process being selective diffusion through a metallic membrane, such as a palladium membrane, one being commercially available as RSI Hydrogen Purifier™, from Resource Systems Inc., East Hanover, N.J.

Methanol is separated from the reaction fluid via standard chemical engineering operations such as fractional distillation, sparging of the methanol with an inert gas, or selective membrane separation.

Typically, approximately 5.5 percent of methane was converted in the process. However, when hydrogen peroxide is added to the reaction fluid, methane conversion rates nearly double (to 9 percent), which confirms that the hydroxyl mechanism plays a major role in the invented process.

Methane Detail

Prior to entering the reaction chamber 16, methane is mixed with water. In as much as water is a necessary reactant in the invented process, per Reaction Scheme 1 supra, a water saturator is often necessary to keep water volume in the reactor 16 constant by preventing water from being blown out of the reactor during methane input. While potable water can be used to effect viable conversion rates, deionized water that is distilled prior to use provides superior results.

The extent of mixture of methane to water can vary from 0.088 weight percent to 0.89 weight percent (i.e., near saturation). In cases where complete water-vapor saturation of methane is desired, a water-vapor saturator 17 is connected, in-line, between the methane supply 12 and the reaction chamber 16. An exemplary water-vapor saturator is disclosed in the K. Ogura paper, noted supra, and incorporated herein by reference. Generally, the water saturator sparges methane through a heated water bath (maintained at a temperature of between approximately 70° C. and 95° C. at atmospheric pressure). Reaction temperatures maintained below the boiling point of water are suitable.

Neat methane feeds typically facilitate industrial-scale processes which do not require continual on-line MS-spectroscopy analysis. However, when small-scale methane conversion processes are employed and to monitor conversion rates, noble fluids are used as carrier gases, including helium, argon, neon, and nitrogen. In such on-line analysis scenarios, a quadrupole mass spectrometer capable of distinguishing between methanol and dioxygen, both of which exhibit a parent peak at 32 atomic mass units (AMU), is utilized.

Reaction pressure inside the reactor 16 can be regulated by the pressure of the methane feed, and generally, feed pressures ranging from 0.03 atmospheres (atm) to 500 atm are suitable.

Light Source Detail

A salient feature of the invented process is its enablement with radiation above approximately 400 nm. This allows for the use of visible light across the spectrum, such as sunlight. In one embodiment of the invented process, a high pressure, quartz mercury-vapor lamp is utilized as the light source 18. In order to separate reactions initiated by radiation with UV light from reactions initiated by visible light, the lamp is enveloped by a filter to facilitate blockage of UV light. One exemplary filter is comprised of a Pyrex® sleeve fitted around the lamp. Surprisingly and unexpectedly, it was found that the sleeve blocks virtually all radiation below approximately 310 nm emanating from the lamp.

While the spectral characteristics of artificial sources vary, generally any light source that provides approximately 30 to 50 percent of its radiation in the visible spectra is suitable. More important than the energy output of the light source 18 is the wavelength of the impinging light on the reaction fluid 20. When a light source 18 having the above spectral characteristics are utilized, radiated energy values of approximately 8 watts produce suitable results. The inventors have found that a standard high pressure quartz lamp outfitted with the filter as discussed supra, provides such wattage. Energy values for unfiltered lamps are approximately 25 watts.

Semi-Conductor Catalyst Detail

Materials which facilitate the swapping of electrons from their valence orbitals are suitable catalysts for the instant method. Generally, any transition metal oxide serves this purpose, in as much as transition metals have one or two electrons in their outermost s sub-shells. Exemplary oxides include tungsten oxide ($WO_3$), bismuth trioxide ($Bi_2O_3$), ruthenium (IV) oxide ($RuO_2$), iron (III) oxide ($Fe_2O_3$), titanium dioxide ($TiO_2$), and cadmium sulfide (CdS).

Dopants added to the metal oxide effect electron transfer, and effective amounts range from between approximately 0.5 atom percent and 10 atom percent. Most preferable dopant amounts are approximately less than 4 atom percent. A number of different elements, listed in decreasing efficiency herein, are suitable dopants and can be selected from the group consisting of titanium, vanadium, chromium, manganese, iron, cobalt, nickel, copper, zinc, ruthenium, lanthanum, lithium, silver and platinum.

Generally, synthesis of the semi-conductor catalyst follows the procedure designated in M. Ashokkumar and P. Maruthamuthu *Journal of Material Science Letters* 1988, 24, 2135–2139, and M. Ashokkumar and P. Maruthamuthu *International Journal of Hydrogen Energy* 14 (4) (1989) pp 275–277, and incorporated herein by reference.

Reaction Fluid Detail

As noted supra, the reaction fluid 20 is comprised of the saturated methane, suspended catalyst, and electron transfer agent. Surprisingly and unexpectedly, when an optional reactant, hydrogen peroxide, is added to the reaction fluid, a near doubling (9 percent) of methane conversion occurs.

Instead of subjecting the methane feed 12 to a water saturation step 17, methane (either neat or mixed with carrier gas) can be added directly into the reaction chamber 16 containing an aqueous solution of electron transfer agent and catalyst.

Which ever methane addition sequence is utilized, ultimately the weight percent of the electron transfer agent to water should be selected from a range of between approximately 0.00025 weight percent and 0.0248 weight percent, and preferably 0.0050 weight percent. The weight percent of catalyst to water should be selected from a range of between approximately 0.066 percent and 0.400 percent, and preferably 0.13 percent. A typical reaction preparation is the addition of 1.000 grams of doped catalyst (i.e. La/WO$_3$)and 0.0400 grams of electron transfer agent (i.e., methyl viologen dichloride hydrate) to 750 ml (approximately 750 grams) of distilled, deionized water.

Experimentation determines the effective weight percent of electron transfer agent to catalyst in the fluid. Generally, however, weight ratios of transfer agent to catalyst selected from a range of between 0.001 and 0.373 is suitable. When methyl viologen dichloride hydrate (1,1'-dimethyl-4,4'-bipyridinium dichloride) is used as the transfer agent, a suitable weight percent of transfer agent to catalyst is approximately 0.045.

Suitable electron transfer agents are selected from the group consisting of 1,4-dicyanobenzene, p-dicyanobenzene, chloranil, 1,4-dicyano-2,3,5,6-tetraethylbenzene, 1-cyanonaphthalene, 2,4,6-trinitrobenzene, hexamethylphosphoric triamide, and methyl viologen dichloride hydrate.

To assure effective contact between reactants and the catalyst, a stirring or agitating mechanism is necessary to keep the catalyst suspended. In laboratory-scale embodiments, a teflon stirring bar provides suitable agitation while in industrial scale situations, any mechanism to effect eddy currents inside the reaction chamber 16 is suitable.

The temperature and pressure of the fluid also is maintained to achieve and sustain effective reaction rates and yields. Reaction temperatures of approximately 70° C. and above produce good results. As noted supra, the temperature can be reached by heating the saturating water prior to methane mixture. Another technique for reaching and maintaining desired reaction temperatures is to equip the reaction chamber with a heating element such as an external recirculating, thermostated bath. An exemplary bath comprises heated (between 90° C. and 130° C.) silicon oil in an outer jacket (not shown) of the reaction chamber 16.

Temperatures also can be maintained as a natural consequence of heat associated with the light source 18. However, with significant amounts of methane conversion (i.e. approximately at least 15 percent) the exothermicity of the reaction may obviate the need for additional heat input, and in fact may require a heat exchange means for diverting heat, which is generated by the light source 18, from the reaction fluid 20.

Conversion rates will vary but usually fall in the range of between approximately 0.67 grams of methanol produced per kilogram of catalyst per hour to 1.5 grams of methanol produced per kilogram of catalyst per hour. A more typical yield is approximately 1.0 gram of methanol produced per kilogram of catalyst per hour.

EXAMPLE

In one embodiment of the invention, a gaseous mixture of methane (at 5 mL/min) and helium (16 mL/min) was utilized as the methane feed 12. The methane feed 12 was mixed with tungsten oxide catalyst doped with lanthanum (4 atomic weight percent) suspended in methyl viologen dichloride hydrate.

Figure 2:
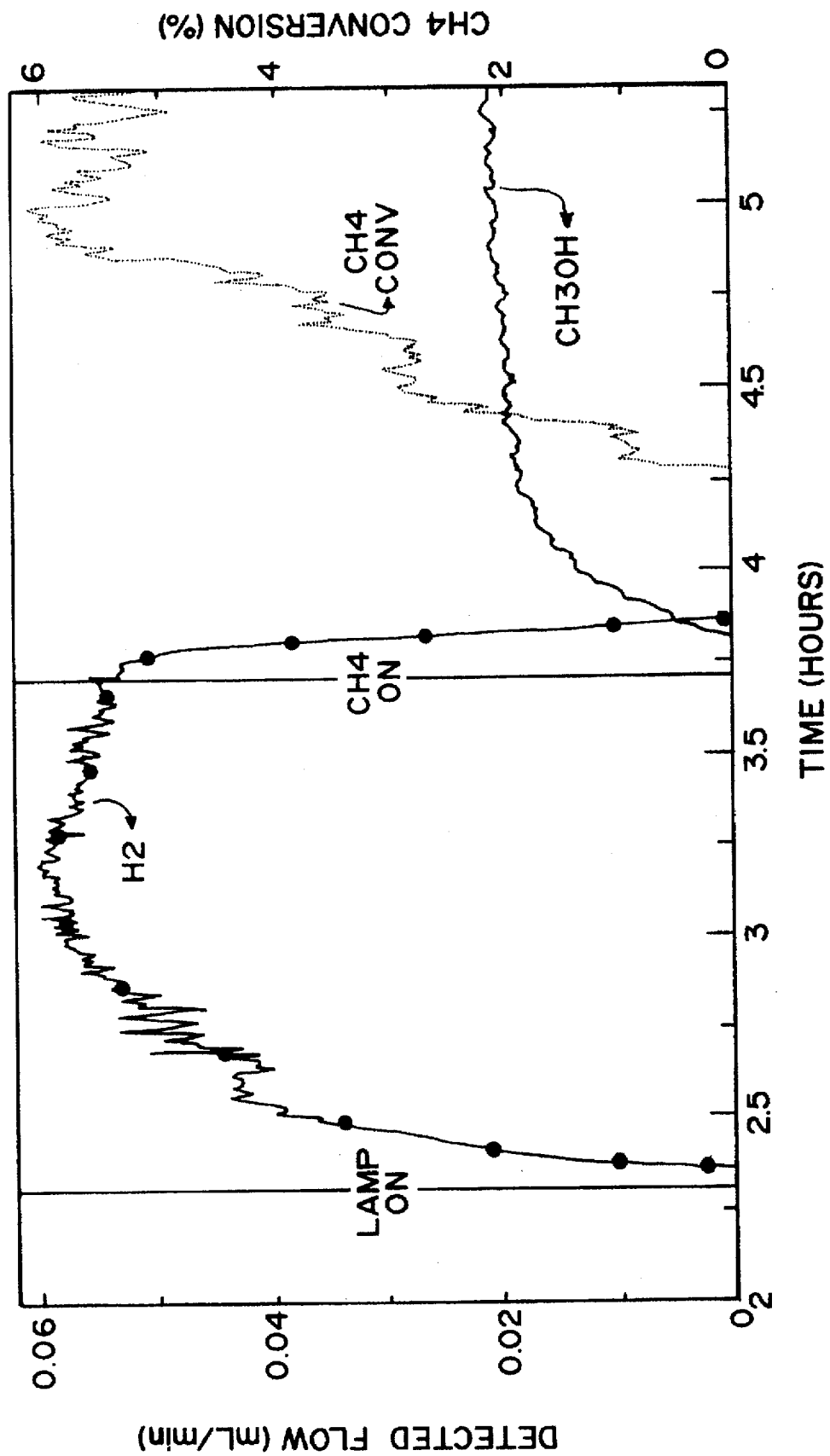
FIG. 2 is a graph showing methane conversion data, in accordance with the present invented method.

As can be noted in FIG. 2, hydrogen production is observed approximately 3 minutes after the light source 18 is turned on. Methanol, carbon monoxide and carbon dioxide are detected approximately 6 minutes after methane flow is started. Methane conversion leveled off at approximately 5.5 percent.

Figure 3:
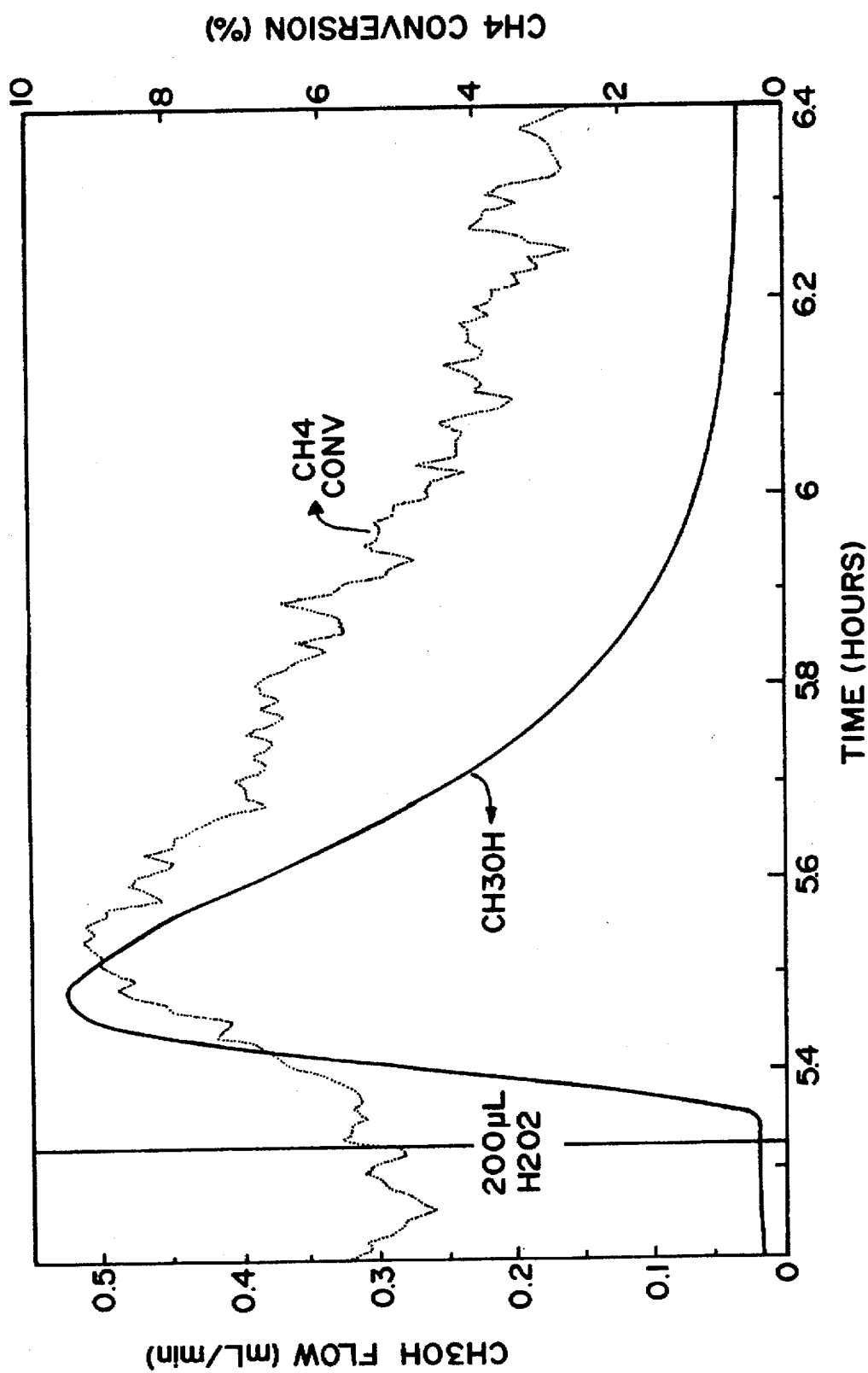
FIG. 3 is a graph showing enhanced methane conversion data, in accordance with the present invented method.

FIG. 3 illustrates the effects of the addition of 200 µL of 30 percent hydrogen peroxide. After $H_2O_2$ addition, methanol production increased 25 fold, carbon dioxide increased 50 fold and methane conversion peaked at 9 percent. Conversions of methane in the presence of hydrogen peroxide were of the order of 43 grams of methanol per gram of catalyst per hour. This is more than 25 times the conversion rate without hydrogen peroxide.

While the invention has been described with reference to details of the illustrated embodiment, these details are not intended to limit the scope of the invention as defined in the appended claims. For example, the invented method could be utilized in configurations whereby sunlight, either natural or focused, impinges on the reactor fluid. Such configurations further decrease capital and operating costs associated with initial process tool up and electricity requirements.

The embodiment of the invention in which an exclusive property or privilege is claimed is defined as follows:

1. A method for converting methane to methanol comprising subjecting a mixture of methane and water to visible light in contact with a transition metal oxide catalyst and an electron transfer agent.

2. The method as recited in claim 1 wherein the methane is pretreated.

3. The method as recited in claim 2 wherein the methane is pretreated by saturating the methane with water.

4. The method as recited in claim 3 wherein the water contains hydrogen peroxide.

5. The method as recited in claim 1 wherein the conversion occurs at a temperature of at least approximately 70° C.

6. The method as recited in claim 1 wherein the visible light has a wavelength of at least approximately 400 nm.

7. The method as recited in claim 1 wherein the conversion occurs at a pressure selected from a range of between approximately 0.03 atmospheres and 500 atmospheres.

8. The method as recited in claim 1 wherein the catalyst contains a dopant selected from the group consisting of titanium, vanadium, chromium, manganese, iron, cobalt, nickel, copper, zinc, ruthenium, lanthanum, lithium, silver, platinum and combinations thereof.

9. The method as recited in claim 1 wherein the transition metal is selected from the group consisting of tungsten, bismuth, ruthenium, iron, cadmium, and combinations thereof.

10. A method for reacting methane and water to produce methanol and hydrogen comprising:
   a) preparing a fluid containing a mixture of methane, an electron transfer agent and a transition metal oxide catalyst; and
   b) subjecting said fluid to visible light for a period of time of between approximately 1 second and 5 minutes.

11. The method as recited in claim 10 wherein the electron transfer agent is selected from the group consisting of methyl viologen dichloride hydrate, 1,4-dicyanobenzene, p-dicyanobenzene, chloranil, 1,4-dicyano-2,3,5,6-tetraethylbenzene, 1-cyanonaph-thalene, 2,4,6-trinitrobenzene, hexamethylphosphoric triamide, and combinations thereof.

12. The method as recited in claim 10 wherein said oxide of a transition metal contains a dopant selected from the group consisting of platinum, lanthanum, copper, and combinations thereof.

13. The method as recited in claim 10 wherein the prepared fluid is maintained at a temperature of at least approximately 70° C.

14. The method as recited in claim 10 wherein the prepared fluid is maintained at a pressure of between approximately 0.03 atmospheres and 500 atmospheres.

15. A method for converting methane to methanol comprising:

a) saturating methane with water;

b) heating the saturated methane to at least approximately 70° C.;

c) mixing the heated, saturated methane with water and effective amounts of a transition metal oxide catalyst and an electron transfer agent to create a reaction fluid; and d) exposing the reaction fluid to visible light.

16. The method as recited in claim 15 wherein the catalyst is tungsten trioxide and the electron transfer agent is methyl viologen dichloride hydrate.

17. The method as recited in claim 16 wherein the catalyst is present in a weight ratio with water of the reaction fluid of approximately 0.13 percent and the electron transfer agent is present in a weight ratio with water of the reaction fluid of approximately 0.006 percent.

18. The method as recited in claim 15 wherein the reaction fluid is exposed to the visible light for a period of time of between approximately 1 second and 5 minutes.

19. The method as recited in claim 1 wherein the visible light has a wavelength of at least approximately 310 nm.

* * * * *